US008097001B2

(12) United States Patent  (10) Patent No.: US 8,097,001 B2
Nakao  (45) Date of Patent: Jan. 17, 2012

(54) MEDICAL INSTRUMENT WITH STOP MOTION OVERRIDE AND ASSOCIATED METHOD

(75) Inventor: Naomi L. Nakao, New York, NY (US)

(73) Assignee: Granit Medical Innovations LLC, New York, NY (US)

( * ) Notice: Subject to any disclaimer, the term of this patent is extended or adjusted under 35 U.S.C. 154(b) by 484 days.

(21) Appl. No.: 11/903,596

(22) Filed: Sep. 24, 2007

(65) Prior Publication Data

US 2009/0082779 A1  Mar. 26, 2009

(51) Int. Cl.
*A61B 17/00* (2006.01)

(52) U.S. Cl. .................................................. 606/114

(58) Field of Classification Search .......... 606/113–115, 606/127–128, 170–171, 185, 1, 110, 139, 606/167, 205; 600/101, 184
See application file for complete search history.

(56) References Cited

U.S. PATENT DOCUMENTS

| 5,653,716 A * | 8/1997 | Malo et al. ............. 606/139 |
| 6,210,398 B1 * | 4/2001 | Ouchi ............................ 606/1 |
| 6,383,197 B1 * | 5/2002 | Conlon et al. ............. 606/114 |

\* cited by examiner

*Primary Examiner* — Ryan Severson
*Assistant Examiner* — Ashley Cronin
(74) *Attorney, Agent, or Firm* — R. Neil Sudol; Henry D. Coleman; William J. Sapone

(57) ABSTRACT

A medical instrument comprises a tubular introducer member, an operative element, an elongate shifter connected at a distal end to the operative element, a handle, at least one stop component, and an override. The shifter and the operative element are movable relative to the tubular member, while the first part of the handle is fixed to a proximal end of the tubular member and the second part of the handle is fixed to a proximal end of the shifter. The stop component is disposed on the first part or second part to limit relative motion of the first part and the second part and concomitantly to stop travel of the operative element at a predetermined location relative to a distal end of the tubular member. The override enables a user to override or passivate the stop component and thereby permit travel of the operative element past the predetermined location.

13 Claims, 3 Drawing Sheets

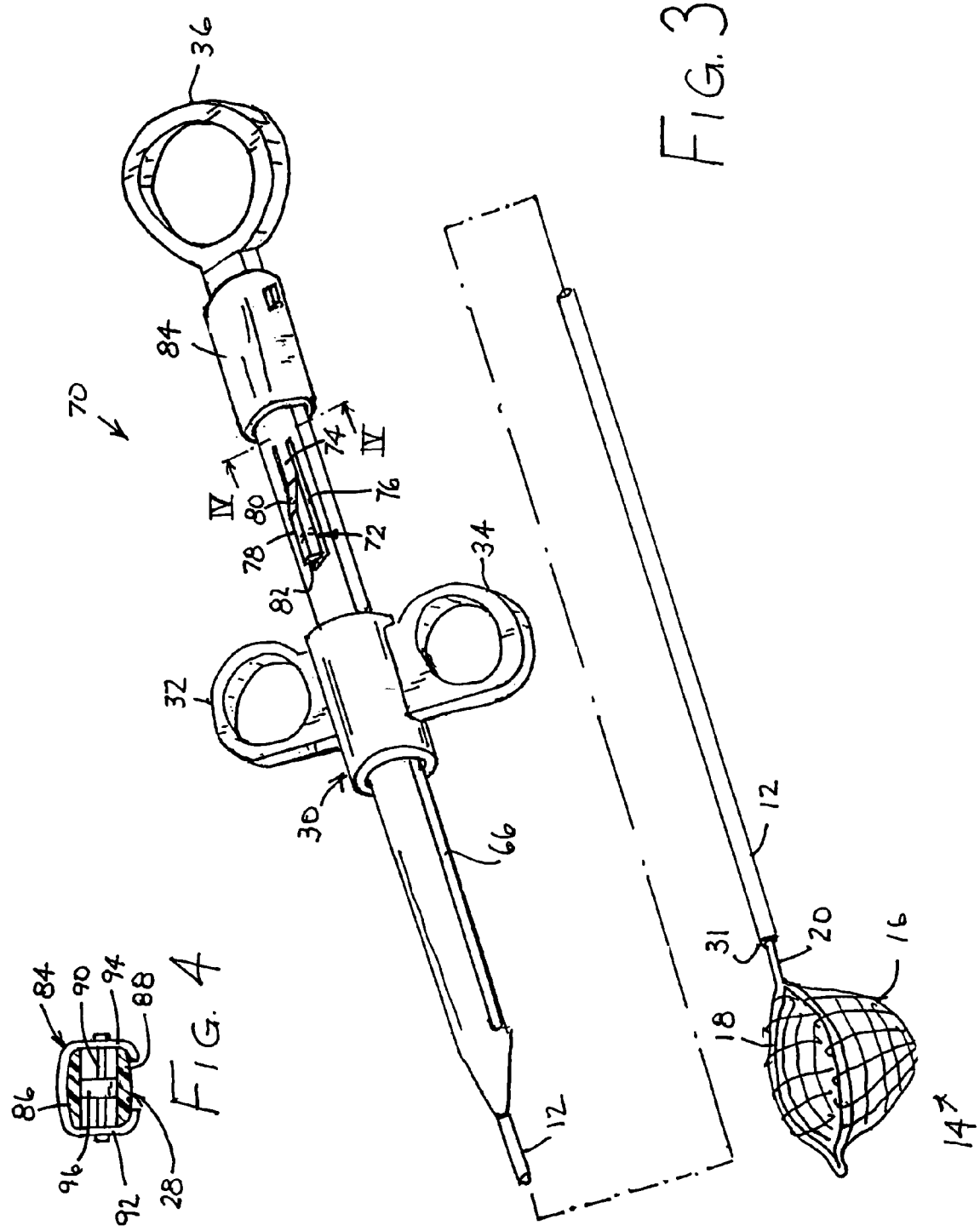

MEDICAL INSTRUMENT WITH STOP MOTION OVERRIDE AND ASSOCIATED METHOD

BACKGROUND OF THE INVENTION

This invention relates to a surgical and diagnostic device wherein an operative element is alternately ejected from and drawn back into the distal end of a tubular introducer member. Such a device is particularly useful in minimally invasive surgery. The operative element may take the form of a specimen retrieval net, a cauterization snare, or other diagnostic or therapeutic structure.

Endoscopic retrieval devices include a tubular introducer sheath, an elongate shifter wire extending through the sheath and carrying a pouch at a distal end. When outside of the introducer sheath, the pouch is held open by a loop. Upon capture of a specimen, the loop and pouch are withdrawn partially into the tubular member to close the pouch and trap the specimen. Sometimes, it is necessary or desirable to extend and open the pouch again. However, if the loop has been retracted in its entirely into the sheath, the nose of the loop can catch on the pouch when the loop is ejected from the tubular member. The loop then buckles and the efficacy of the pouch is compromised. This catching of the loop nose on the pouch and the buckling of the loop happen particularly when the device includes a tether that causes the net to bunch up when the retrieval loop and pouch are being withdrawn into the tubular sheath. Cauterization snares with such tethers are disclosed in U.S. Pat. No. 5,759,187.

OBJECTS OF THE INVENTION

It is an object of the present invention to provide an improved medical instrument of the above-described type.

Another object of the present invention is to provide a medical instrument or device with means for controlling or limiting the motion of an operative element relative to a distal end of a tubular introducer sheath.

A further object of the present invention is to provide such a medical instrument or device wherein the limitation or stop on the relative motion of the operative element may be overridden, as warranted, by the user.

Another, important, object of the present invention is to enable a manual override of the stop with the operator using the same hand that holds and operates the medical instrument. Thus, the entire function of the medical instrument can be executed with one hand.

Yet another object of the present invention is to provide such a medical instrument or device wherein the overriding of the stop may be accomplished manually, with sufficient leverage, without catching or pinching a surgical glove worn by the user.

Yet a further object of the present invention is to provide an associated method for use in medical diagnostic or therapeutic procedures.

These and other objects of the invention will be apparent from the drawings and descriptions herein. Although every object of the invention is deemed to have been met by at least one embodiment of the invention, there is not necessarily any one embodiment that achieves all of the objects of the invention.

SUMMARY OF THE INVENTION

A medical instrument comprises, in accordance with the present invention, a tubular member, an operative element, an elongate shifter connected at a distal end to the operative element, a handle, at least one stop component, and an override. The shifter and the operative element are movable relative to the tubular member, while first part of the handle is fixed to a proximal end of the tubular member and a second part of the handle is fixed to a proximal end of the shifter. The stop component is disposed on the first part or second part to limit relative motion of the first part and the second part and concomitantly to stop travel of the operative element at a predetermined location relative to a distal end of the tubular member. The override enables a user to override or passivate the stop component and thereby permit travel of the operative element past the predetermined location.

Preferably, the override includes a spring loading of the stop component.

In one embodiment of the present invention, the override further includes a tapered form of the stop component. More particularly, where the stop component is disposed on one handle part, the tapered form includes an inclined or beveled surface that faces the other handle part. The tapered form is so spring-loaded as to provide an increased resistance to relative motion of the two handles parts when the operative element has reached the predetermined location. Thus, the user can sense through tactile or kinesthetic sensations that the handle stop has been reached and that the operative element has reached the predetermined end of a range of motion. Pursuant to the exigencies of the situation, the user can simply override the stop by exerting a greater force on the handle parts, to overcome the increased resistance offered by the stop component. This is necessary, for instance, in an initial loading of the operative element into the distal end of the tubular member.

The second handle part typically includes two opposed rings for receiving an index finger and middle finger of a user and the first handle part concomitantly includes an additional ring for receiving the thumb of the user. In that case, the stop component is preferably disposed on the second part.

In another embodiment of the present invention, the override includes a slidable member. The slidable member is located on the same handle part as the stop component. The slidable member may take the form of a sleeve.

In a further embodiment of the present invention, the stop component is disposed on an elongate resilient element fastened at a proximal end to the first handle part. The spring loading of the stop component is implemented by the inherent spring bias of the polymeric material of the elongate resilient element. The first handle part is formed with an elongate opening, and at least a portion of the elongate resilient element extends longitudinally parallel to and in alignment with the opening. At least a distal end portion of the elongate resilient element and the stop component have a width narrower than a width of a distal end portion of the opening, so that a manual pressing of the elongate resilient element towards the first part shifts the distal end portion of the stop component into the opening.

A medical method, in accordance with the present invention, utilizes a medical instrument including a tubular member and an operative element connected to a distal end of an elongate shifter extending through the tubular member, the medical instrument further including a handle having a first part and a second part movable relative to one another, the first part being fixed to a proximal end of the tubular member, the second part being fixed to a proximal end of the shifter. The method additionally comprises moving the second handle part in a given direction relative to the first handle part, thereby moving the operative element in that given direction relative to the tubular member. During the moving of the second handle part, a stop component on the first handle part is engaged by the second part, thereby limiting or arresting continued motion of the operative element relative to the tubular member at a predetermined stop location. Subsequently, one overrides or passivates the stop component. During or after this overriding or passivating of the stop component, one continues to move the second handle part in the proximal direction relative to the first part, thereby moving the operative element in a proximal direction relative to the tubular member past the predetermined location.

Pursuant to another feature of the present invention, the overriding or passivating of the stop component includes shifting the stop component. Preferably, the shifting of the stop component is in opposition to a spring force and may be in a direction substantially orthogonal to a direction of motion of the second handle part relative to the first handle part.

The shifting of the stop component may more particularly include moving the second part against an inclined surface of the stop component, the shifting of the stop component being a camming motion thereof arising from engagement of the second part with the inclined surface. Alternatively, the shifting of the stop component may include moving a slidable member along the first part so that the slidable member engages an inclined surface of the stop component, the shifting of the stop component again being a camming motion thereof arising from engagement of the slidable member with the inclined surface.

In a further alternative approach, the stop component is provided on a distal or free end of an elongate resilient element attached to or integral with said first part. The shifting of the stop component includes exerting a force on a rear or proximal portion of the elongate resilient element at a point substantially spaced from the stop component, to shift the stop component into an opening provided in the first handle member. Because the override actuation force is applied to the resilient member at a point spaced from the stop, there is no chance that a glove worn by the user would become pinched or caught upon movement of the second handle part past the stop.

BRIEF DESCRIPTION OF THE DRAWINGS

FIG. 3 is a schematic partial perspective view of a medical instrument with a modified motion stop or excursion limiter having a modified manual override means, in accordance with the present invention.

FIG. 4 is a partial transverse cross-sectional view taken along line IV-IV in FIG. 3.

Features having the same structure and function in FIGS. 1-3 are designated with the same reference numerals.

DETAILED DESCRIPTION

Figure 1:
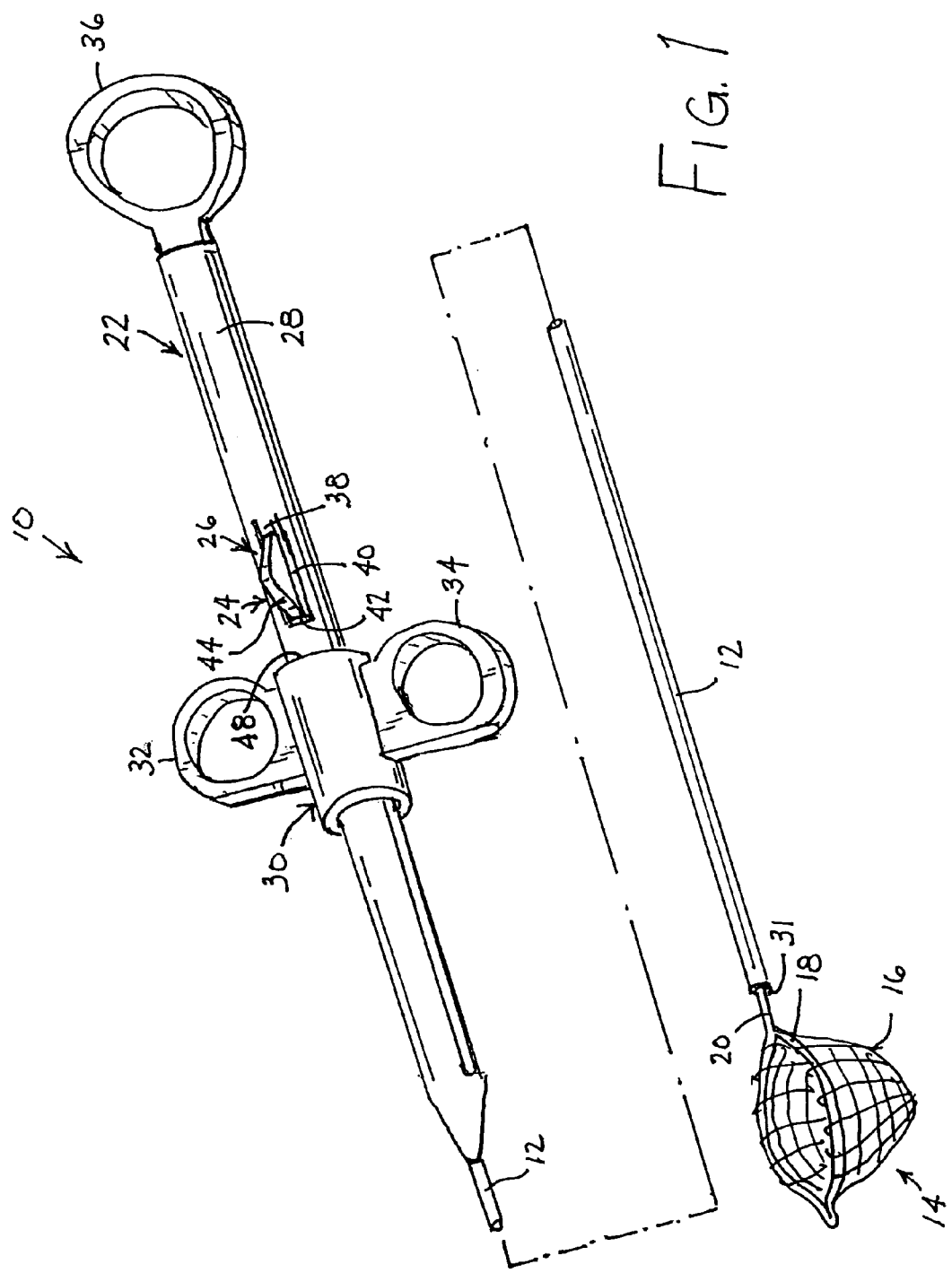
FIG. 1 is a schematic partial perspective view of a medical instrument with a motion stop or excursion limiter having manual override means, in accordance with the present invention.

As depicted in FIG. 1, an endoscopic or laparoscopic medical instrument 10 comprises a tubular introducer sheath 12, an operative element 14 such as a specimen retrieval pouch 16 on a loop 18, an elongate shifter 20 connected at a distal end to the operative element, a handle 22, at least one stop component 24, and an override 26. Shifter 20 and operative element 14 are movable relative to tubular sheath 12. Handle 22 has a first part 28 fixed to a proximal end of tubular sheath 12 and a second part 30 fixed to a proximal end of shifter 20. Stop component 24 is disposed on first handle part 28 to limit relative motion of the handle parts 28 and 30 and concomitantly to stop travel of the operative element 14 at a predetermined location relative to a distal end 31 of tubular sheath 12. Override 26 enables a user to override or passivate stop component 24 and thereby permit travel of operative element 14 past the predetermined location.

Handle part 30 includes two opposed rings 32 and 34 for receiving an index finger and middle finger of a user, while handle part 28 concomitantly includes an additional ring 36 for receiving the thumb of the user.

Stop component 24 takes the form of a protrusion disposed on a spring-loaded tongue 38. Cutting an elongate U-shaped slot 40 in handle part 28 forms tongue 38. Handle parts 28 and 30 are typically made of a substantially rigid material that is sufficiently resilient to permit a free end 42 of tongue 38 to be pressed inwardly into handle part 28. This transverse shifting of tongue free end 42 in opposition to a biasing or return force exerted by tongue 38 enables the override function.

Stop protrusion 24 has a beveled or tapered form at least on a distal side, facing handle part 30. More specifically, stop protrusion 24 has an inclined surface 44 that functions as a camming surface converting a rearward linear motion of handle part 30 into a transverse or radial shifting of tongue 38 and protrusion 24 and enabling a continued proximal movement of handle part 30 relative to handle part 28.

The spring bias of mounting tongue 38 provides enough resistance to the inward shifting of protrusion 24 that, during a proximal motion of handle part 30 relative to handle part 28, a user can sense the increased resistance once a rear edge 48 of handle part 30 comes into contact with inclined surface 44 of protrusion 24. The user then knows the position of operative element 14 relative to distal end 31 of tubular sheath 12. Should circumstances warrant, for example, during factory loading of operative element 14 into sheath 12, the user can continue moving handle part 30 in a proximal direction relative to handle part 28, shifting tongue end 42 and protrusion surface 44 inwardly so that protrusion 24 slides under rear edge 48.

Thus, override 26 includes a spring loading of stop protrusion 24, as well as the beveled or tapered form of protrusion 24. These features enable a user to move operative element 14 past a predetermined stop or excursion limit, as warranted. In addition, the stop and override structure of FIG. 1 enables the user to operate instrument 10 and engage the stop and override functions using only one hand. The user need not touch stop protrusion 24, so it is not possible for a glove to become pinched between moving handle parts 28 and 30.

In another embodiment of the present invention, the override includes a slidable tab member. The tab member is located on the same handle part as the stop component.

In using the instrument 10 of FIG. 1, after operative element 14 has been deployed in an extended position, one might wish to retract the operative element into tubular sheath 12. One moves handle part 30 proximally relative to handle part 28, thereby moving operative element 14 in that same direction relative to tubular sheath 12. During the moving of handle part 30, protrusion 24 is engaged by rear edge 48 of part 30, thereby limiting or arresting continued motion of operative element 14 relative to tubular sheath 12 at a predetermined stop location. Subsequently, one continues with increased force to move handle part 30 in the proximal direction relative to part 28, thereby overriding the resistance provided by stop protrusion 24 and moving operative element 14 in the proximal direction relative to sheath 12 past the predetermined location.

As indicated above, the overriding of stop protrusion 24 is implemented by shifting the stop protrusion transversely and inwardly relative to handle part 28. The shifting of stop protrusion 24 is in opposition to an inherent spring force exerted by tongue 38 and is, more particularly, in a direction substantially orthogonal to a direction of motion of handle part 30 relative to handle part 28.

Figure 2:
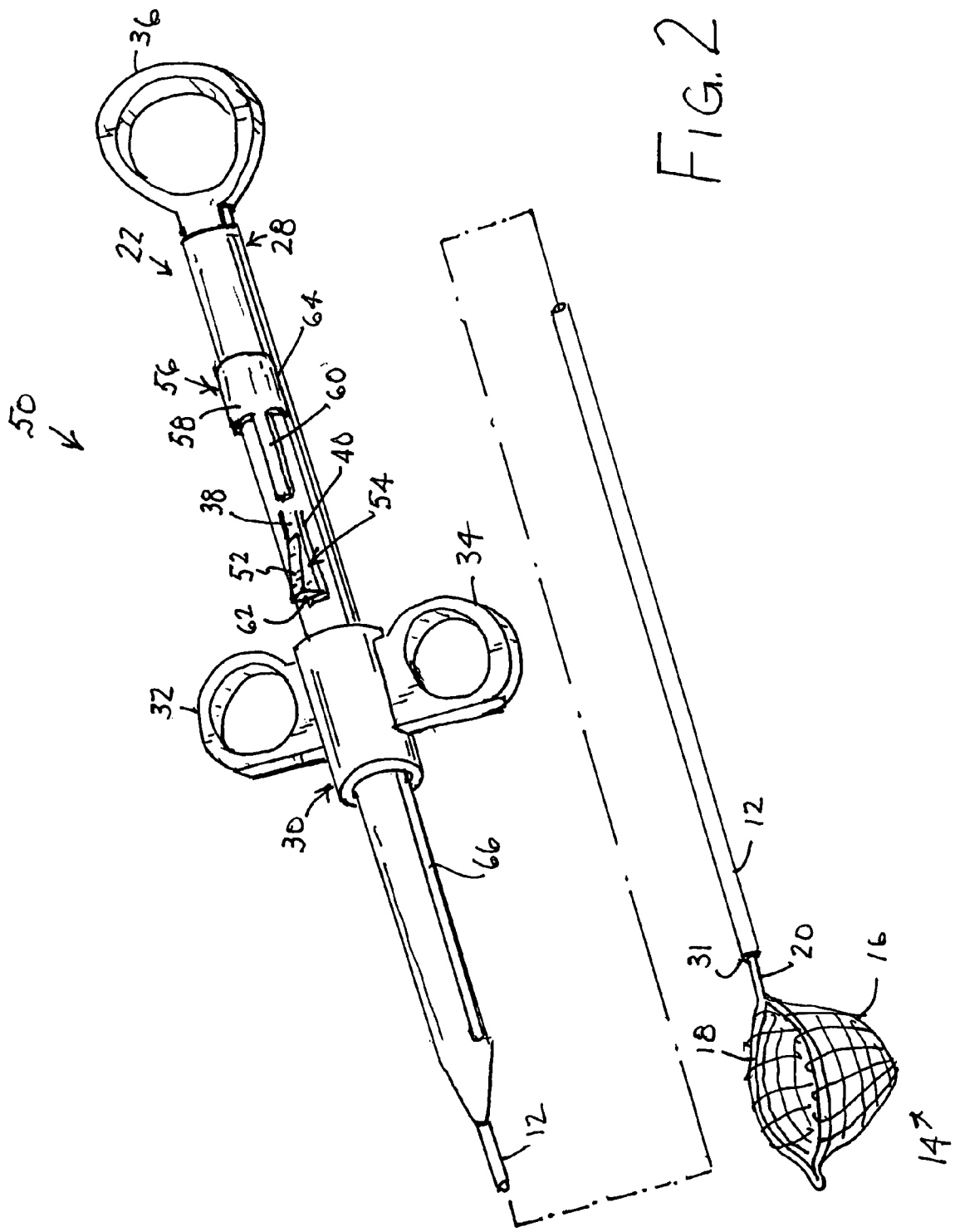
FIG. 2 is a schematic partial perspective view of a medical instrument with another motion stop or excursion limiter having manual override means, in accordance with the present invention.

FIG. 2 depicts another endoscopic or laparoscopic medical instrument 50 and uses the same reference numerals for the same parts shown in FIG. 1. FIG. 2 depicts a stop component 54 in the form of a wedge with a beveled or inclined surface 52 facing in a proximal direction, away from handle part 30. Override 56 enables a user to override stop component 54 and thereby permit travel of operative element 14 past the predetermined location.

Stop wedge 54 is disposed on spring-loaded tongue 38. Again, one forms tongue 38 by cutting U-shaped slot 40 in handle part 28.

Override 56 takes the form of slide having a slotted-sleeve body 58 and a distally projecting finger or tab 60. Override sleeve 58 has a pair of longitudinal wings 64 (only one shown) that insert into respective lateral longitudinal slots 66 in handle part 28. When a user wishes to override the stop action of wedge 54, he or she pushes override slide 56 forward so that finger 60 engages inclined surface 52 and causes wedge 54 and tongue 38 to shift inwardly into handle part 28 out of a path of handle part 30 so that rear edge 48 of handle part 30 can move over a leading end 62 of top wedge 54. Override slide 56 is different from handle parts 28 and 30 and movable with respect to both of those components.

Inclined surface 52 functions as a camming surface converting a forward linear motion of override slide 56 into a transverse or radial shifting of tongue 38 and wedge 54 and enabling a continued proximal movement of handle part 30 relative to handle part 28.

The spring bias of mounting tongue 38 in the embodiment of FIG. 2 need be only enough to ensure that leading or proximal end 62 is raised and in the travel path of part 30, absent the override action of slide 56.

It is possible for a user to operate override slide 56 using only one hand. The user removes his or her thumb from thumb ring 36 and holds the thumb ring against the palm of the hand. The thumb can then push override slide alternately forwards and backwards. The thumb does not approach handle member 30 so there is no chance that a glove will become caught in between parts 28 and 30. Otherwise, the use of instrument 50 is the same as the use of instrument 10.

FIG. 3 depicts another endoscopic or laparoscopic medical instrument 70 and uses the same reference numerals for the same parts shown in FIGS. 1 and 2. FIG. 3 shows a stop component 72 as an enlarged distal end portion of an elongate resilient finger 74. Finger element 74 may be formed by cutting an elongated U-shaped slot 76 in a proximal end of handle part 28 and by attaching stop component 72 to the free end of finger 74. Stop component 72 includes a prismatic distal end portion 78 and a tapered or inclined proximal wedge portion 80. Stop component 72 may be attached to finger element 72 by adhesive or thermally bonding or ultrasonically welding.

In FIG. 3, finger element 74 extends longitudinally parallel to and aligned with an elongate, longitudinally oriented, rectangular opening or cutout (not separately labeled) in handle part 28, the opening or cutout being defined or formed by slot 76. Finger element 74 has an inherent spring bias tending to maintain the finger element in the parallel configuration, whereby stop component 72, particularly a transversely oriented distal end face 82 of stop component 72, is disposed in a travel path of handle part 30 and thus prevents that handle part from being drawn in a rearward direction beyond the stop component 72.

A manually operable slotted override sleeve 84 is slidably mounted to handle part 28 to enable a user to pull handle part 30 in a distal direction past end face 82 of stop component 72. Override sleeve 84 accomplishes this by shifting stop component 72 inwardly in a direction substantially orthogonal to the direction or path of motion of handle part 30 relative to handle part 28. Stop component 72 and at least an associated distal end portion of resilient finger element 74 have a width narrower than a width of a distal end portion of the opening or cutout defined by slot 76, so that a pressing of stop component 72 towards handle part 28 is able to shift stop component 72 and resilient finger element 74 into the opening or cutout. Override sleeve 84 is different from handle parts 28 and 30 and movable with respect to both of those components.

As depicted in FIG. 4, stop override sleeve 84 extends around handle part 28, particularly including two spaced slats 86 and 88 thereof. Override sleeve 84 is provided with a cross-bar or rod 90 that extends between two legs or sidewall portions 92 and 94 of the override sleeve. Cross-bar or rod 90 serves to arrest the forward motion of sleeve 84 so that a proximal end 92 of sleeve 84 falls short (by a few millimeters) of stop-component end face 82 at a most-proximal position of sleeve 84. To stop the forward excursion of sleeve 84, crossbar or rod 90 cooperates with a transverse web 96 extending between handle part slats 86 and 88.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:
1. A medical instrument comprising:
a tubular member;
an operative element;
an elongate shifter connected at a distal end to said operative element, said shifter and said operative element being movable relative to said tubular member;
a handle having a first part and a second part movable relative to one another, said first part being fixed to a proximal end of said tubular member, said second part being fixed to a proximal end of said shifter;
at least one stop component disposed on said first part and engageable with said second part to limit relative motion of said first part and said second part and concomitantly to stop travel of said operative element at a predetermined location relative to a distal end of said tubular member; and
an override member slidably disposed on said first part and engageable with said stop component for enabling a user to so shift said stop component out of a travel path of said second part as to enable travel of said operative element past said predetermined location, said override member being different from and movable with respect to both said first part and said second part, said override member being linearly slidable or translatable relative to said stop component.

2. The medical instrument defined in claim 1 wherein said stop component is spring-loaded.

3. The medical instrument defined in claim 2 wherein said stop component includes a beveled or inclined surface engageable with said override member so that a sliding movement of said override member against said beveled or inclined surface shifts said stop component transversely out of said travel path in a camming action.

4. The medical instrument defined in claim 2 wherein said stop component is disposed on an elongate resilient element on said first part, the spring loading of said stop component being implemented by said elongate resilient element, said first part being formed with an elongate opening, at least a portion of said elongate resilient element extending longitudinally parallel to and in alignment with said opening, at least a distal end portion of said elongate resilient element and said stop component having a width narrower than a width of a distal end portion of said opening, so that a manual pressing of said elongate resilient element towards said first part shifts said distal end portion of said elongate resilient element and said stop component into said opening.

5. The medical instrument defined in claim 1 wherein said second part includes two opposed rings for receiving an index finger and middle finger of a user and said first part includes an additional ring for receiving the thumb of the user.

6. The medical instrument defined in claim 5 wherein said operative element includes a specimen retrieval pouch.

7. The medical instrument defined in claim 1 wherein said override member at least in part takes the form of a sleeve.

8. The medical instrument defined in claim 1 wherein said override member is slidable parallel to said shifter and alternately in a proximal direction and in a distal direction along said first part.

9. A medical instrument comprising:
a tubular member;
an operative element;
an elongate shifter connected at a distal end to said operative element, said shifter and said operative element being movable relative to said tubular member;
a handle having a first part and a second part movable relative to one another, said first part being fixed to a proximal end of said tubular member, said second part being fixed to a proximal end of said shifter; and
at least one stop component disposed on said first part and engageable with said second part so as to limit motion of said second part relative to said first part and concomitantly to stop travel of said operative element at a predetermined location relative to a distal end of said tubular member,
said stop component having an inclined or beveled camming surface engageable with said second part, during motion of said first part and said second part relative to one another,
said first part being slidably inserted into said second part, said inclined or beveled camming surface facing outwardly and in a distal direction, said first part, said second part and said stop component being so configured that said stop component can be moved inwardly into said first part and out of a travel path of said second part to enable travel of said operative element past said predetermined location, solely by virtue of motion of said second part in a proximal direction relative to said first part.

10. The medical instrument defined in claim 9 wherein said second part includes two opposed rings for receiving an index finger and middle finger of a user and said first part includes an additional ring for receiving the thumb of the user.

11. The medical instrument defined in claim 10 wherein said operative element includes a specimen retrieval pouch.

12. The medical instrument defined in claim 9 wherein said stop component is spring loaded to bias said stop component into a position in the travel path of said second part.

13. The medical instrument defined in claim 12 wherein said stop component is so spring loaded as to provide an increased resistance to relative motion of said first part and said second part when said operative element has reached said predetermined location.

* * * * *